United States Patent

Newham

[11] Patent Number: 6,025,782
[45] Date of Patent: Feb. 15, 2000

[54] DEVICE FOR MONITORING THE PRESENCE OF A PERSON USING PROXIMITY INDUCED DIELECTRIC SHIFT SENSING

[76] Inventor: Paul Newham, 707 Cypresstree, San Antonio, Tex. 78245

[21] Appl. No.: 08/871,363

[22] Filed: Jun. 9, 1997

Related U.S. Application Data

[63] Continuation-in-part of application No. 08/708,397, Sep. 4, 1996, abandoned.

[51] Int. Cl.[7] .................................................. G08B 21/00
[52] U.S. Cl. ...................... 340/573.1; 200/600; 307/116; 307/125; 340/568.1; 340/666
[58] Field of Search ..................................... 340/573, 666, 340/568, 573.1, 568.1; 307/116, 125; 200/600; 439/37, 180

[56] References Cited

U.S. PATENT DOCUMENTS

| | | | |
|---|---|---|---|
| Re. 29,896 | 1/1979 | Gilcher | 340/562 |
| 4,020,482 | 4/1977 | Feldl | 340/573 |
| 4,033,332 | 7/1977 | Hardway, Jr. et al. | 600/535 |
| 4,196,425 | 4/1980 | Williams, Jr. et al. | 340/573 |
| 4,212,295 | 7/1980 | Snyder | 340/573 |
| 4,228,426 | 10/1980 | Roberts | 340/573 |
| 4,242,672 | 12/1980 | Gault | 340/573 |
| 4,293,852 | 10/1981 | Rogers | 340/568 |
| 4,381,788 | 5/1983 | Douglas | 128/722 |
| 4,402,560 | 9/1983 | Swainbank | 339/11 |
| 4,474,185 | 10/1984 | Diamond | 128/722 |
| 4,484,043 | 11/1984 | Musick et al. | 200/85 R |
| 4,565,910 | 1/1986 | Musick et al. | 200/85 R |
| 4,583,084 | 4/1986 | Henderson et al. | 340/573 |
| 4,700,180 | 10/1987 | Vance | 340/573 |
| 4,907,845 | 3/1990 | Wood | 340/573 |
| 5,010,772 | 4/1991 | Bourland et al. | 73/862.046 |
| 5,086,291 | 2/1992 | Schwab, Jr. | 340/604 |
| 5,107,855 | 4/1992 | Harrington et al. | 128/721 |
| 5,144,284 | 9/1992 | Hammett | 340/573 |
| 5,184,112 | 2/1993 | Gusakov | 340/573 |
| 5,235,319 | 8/1993 | Hill et al. | 340/573 |
| 5,253,656 | 10/1993 | Rincoe et al. | 128/782 |
| 5,410,207 | 4/1995 | Joseph et al. | 340/573 |
| 5,448,996 | 9/1995 | Bellin et al. | 128/671 |

Primary Examiner—Glen Swann
Attorney, Agent, or Firm—Kammer & Huff, PLLC

[57] ABSTRACT

A capacitive array is housed within a polyester mat or other appropriate nonconductive substrate material which is interconnected with a control module. The control module supplies to the capacitive array a suitable oscillator driver current and concurrently senses capacitance value changes within the capacitive array induced through dielectric shifts within the array brought about by the proximity or absence thereof of the patient's body mass. The control module consists of a power supply, a driver/sensor circuit, a calibration/comparator logic circuit, a system interconnection integrity circuit, and an alarm generation circuit. It may also optionally contain a nurse call relay circuit for interconnection to a facility's nurse call system.

7 Claims, 3 Drawing Sheets

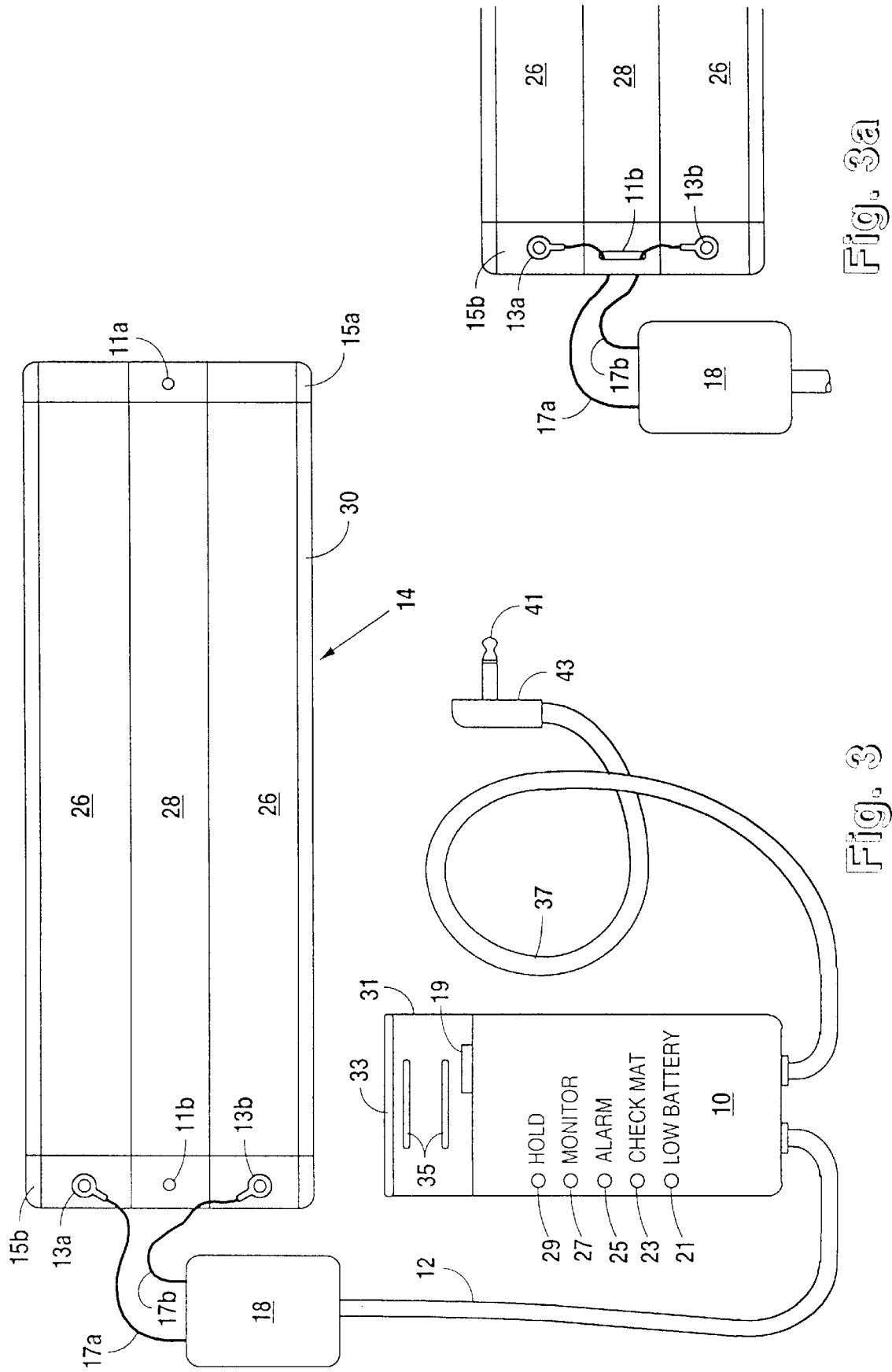

DEVICE FOR MONITORING THE PRESENCE OF A PERSON USING PROXIMITY INDUCED DIELECTRIC SHIFT SENSING

RELATED APPLICATIONS

The present application is a continuation-in-part of co-pending U.S. patent application Ser. No. 08/708,397, filed Sep. 4, 1996, now abandoned, the disclosure of which is incorporated herein by reference.

BACKGROUND OF THE INVENTION

1. Field of the Invention

The present invention relates generally to devices for the detection of dielectric shift induced capacitive changes. The present invention relates more specifically to the use of such devices for the detection and monitoring of the presence or absence of a person from a medical bed, chair or other support structure so as to insure the safety of a patient occupying such a structure.

2. Description of the Related Art

A problem well know to medical service providers is that of making sure certain patients remain in their medical bed or chair. Reasons for this include the need to quickly locate the patient, administer medical treatment to the correct patient, and the prevention of patient injury. Such knowledge is particularly important when patients have become disoriented due to illness or medication.

Medical bed and chair occupancy monitoring systems have been devised to assist medical providers with monitoring the presence or absence of a person in their bed or chair. Such systems typically are equipped with an alarm or are electronically tied to a common monitoring location, such as a nurses station. Such systems principally use some form of pressure sensitive switch as their key sensing element. U.S. Pat. Nos. 4,484,043 and 4,565,910, both Musick et al, and other similar patents describe switch mechanisms which are used to open and close a circuit to indicate the evacuation of a bed or chair by a patient. In the above described patents, the switch apparatus is housed in a thin rectangular cover which may be placed between the patient and the mattress or between the patient and the seating surface. An alternative version of the above described switch mechanism is placed between the lower surface of the mattress and the upper surface of the bed frame. The switch devices in all of the above described mechanisms are each comprised of two rectangular conductors which run the length of the device, are parallel to each other and lie one on top of the other. The two conductors are separated at both ends by a pliable material such as foam and are held apart from each other through the rigidity of the switching apparatus itself. The switch is activated by the pressure of the patient's body weight on the device, either directly thereon or indirectly through the mattress. Once this weight is applied, the two conductive elements come into contact, the switch is closed, and the system indicates that the patient is in the bed or chair. When the switch is opened by the absence of the patient's weight in the bed or chair, the system then sounds an alarm or sends a signal to the medical facility call system through an appropriate interface.

Such pressure sensitive switching elements, as previously described, suffer from certain inherent problems. Switching elements which are placed under the mattress exhibit extremely limited sensitivity and selectivity in identifying the presence of a patient in the bed. This is due to the fact that the patient's weight in the bed is masked by the mattress itself. This masking effect tends to result in frequent false alarms due to the switch failing to close properly, as well as the failure to generate an alarm when the switch fails to open, even though the patient is no longer in the bed. As for pressure sensitive switches placed between the patient and the mattress or seating surface, they must be extremely thin to afford the patient a reasonable degree of comfort. Although such switches exhibit substantially improved sensitivity and selectivity, the required thinness of the movable switch elements, their supportive structure and the required dielectric space between them causes them to have a considerably limited life. Such switches are, therefore, manufactured as disposal devices whose costs prohibit their broad acceptance and use.

It is, therefore, an object of this invention to provide a proximity induced non-compressive dielectric shift sensing device, which replaces the existing pressure sensitive switches previously described for the monitoring of the presence of a patient in a medical environment. A further object of this invention is to provide such a device which either interfaces with occupancy monitoring control modules already in use or utilizes self-contained control module circuitry and controls.

It is another object of the present invention to provide a proximity induced non-compressive dielectric shift sensing device which may be used as a portable unit, or may be wholly or partly built into or mounted on a medical bed, chair, mattress, cushion or similar structure to sense the presence or absence of a person normally occupying the structure.

It is a further object of the present invention to provide a proximity monitoring device with a limited and controlled range that can reliably detect the presence or absence of a person, thereby decreasing the number of false and unreliable alarms.

It is another object of the present invention to provide a proximity monitoring device which will greatly decrease or eliminate patient discomfort by replacing mechanical pressure sensitive switches in the medical bed or chair with a considerably thinner and more flexible sensing element.

It is a further object of this invention to provide a proximity monitoring device, the sensing element of which will exhibit considerably lengthened service life through the elimination of all moving components within the sensing element.

It is a further object of this invention to provide a proximity monitoring device whose sensing element is inherently simpler in design and to manufacture, and utilizes less raw material, thereby resulting in a lower cost end user product.

Additional objects, advantages and novel features of the invention will be set forth in part in the description which follows, and in part will become apparent to those skilled in the art upon examination of the following, or may be learned by practice of the invention. The objects and advantages of the invention may be realized and attained by means of the instrumentalities and combinations particularly pointed out in the appended claims.

SUMMARY OF THE INVENTION

According to the present invention, the foregoing and other objects and advantages are attained by an electronic device able to detect and monitor the presence or absence of a person within a pre-defined space. The device generally comprises a capacitive array housed within a polyester mat or other appropriate nonconductive substrate material which is interconnected with a control module. The control module supplies to the capacitive array a suitable oscillator derived driver current and concurrently senses capacitance value changes within the capacitive array induced through dielectric shifts within the array brought about by the proximity or absence thereof of the patient's body mass. The monitor/control module generally comprises a power supply, a driver/sensor circuit, a comparator/calibration logic circuit, a system interconnection integrity circuit and an alarm generation circuit. It may also optionally contain a nurse call relay circuit for interconnection to a facilities nurse call system.

The driver/sensor circuit provides and senses a suitable current to the capacitive array located in the patient's bed or chair. The driver/sensor circuit is connected to and controlled by a comparator/calibration logic circuit that is most preferably microprocessor based. This logic circuit continually analyzes and optimizes signals received from and generated by the driver/sensor circuit. In this way, the logic circuit defines capacitive value parameters which it interprets to indicate whether a patient is in close proximity to the capacitive array or absent from that array. In such manner, the logic circuit determines the presence or absence of a patient from his or her support structure. Should the capacitive value change and remain at a level indicative of a patient's absence from their support structure, the logic circuit would, after a suitable pre-programmed time delay, instruct an alarm circuit to activate. This alarm activation may consist solely of audible and/or visible alarms on or within the control module or may be directed to a medical facility's nurse call system through an appropriate interface relay circuit contained either within, or remote to, the control module.

In addition to the above described functions, the logic circuit receives continuous data from the control module system interconnection integrity circuit about the continuity of connection between the control module and the capacitive sensor array and, where appropriate, between the control module and the medical facility's nurse call system.

The logic circuit may also, if appropriate, continuously monitor the entire system during utilization for service faults and subsequently generate appropriate alarms.

The apparatus of the invention, uses a proximity induced noncompressive dielectric shift sensing mechanism, and thus reliably detects the presence of absence of a patient from a bed, chair or other support structure, with minimal discomfort to the patient and with a greatly extended sensor element service life.

Still other objects and advantages of the present invention will become readily apparent to those skilled in this art from the following detailed description, wherein multiple preferred embodiments of the invention are shown and described, simply by way of illustration of the best mode contemplated by the inventor for carrying out the invention. As will be realized, the invention is capable of other and different embodiments, and its several details are capable of modifications in various obvious respects, all without departing from the invention. Accordingly, the drawings and descriptions are to be regarded as illustrative in nature, and not as restrictive.

BRIEF DESCRIPTION OF THE DRAWING

FIG. 3 is a plan view of the structures of the various components of the present invention.

FIG. 3a is a plan view of an alternative strain-relief structure and function for the mat of the present invention.

DESCRIPTION OF THE PREFERRED EMBODIMENT

As generally described above, the device of the present invention has practical application in a number of situations. The device may be used to monitor the presence of a person, or animal, within a pre-defined space. The invention described may be used in hospitals or other medical facilities to monitor the occupancy of medical beds, chairs or other supportive structures whenever it may be useful to determine the status of occupancy of such structures. In addition to its use as a stand alone system in combination with such structures, it is possible that the sensing element capacitive array, through its inherently long service life, could be embedded in or under the surface materials of bed mattress covers and seating surfaces. In such fashion a medical facility would then only have to supply and interconnect the control/monitor module component. Equivalently, if appropriate, the entire monitoring system could become an integral component of an appropriate medical bed or chair on a permanent basis either by original manufacture or by retrofit.

Outside the hospital area, the present device may be used in nursing homes, intermediate and long-term care facilities, mental hospitals, and other similar institutions needing to track the presence of individuals. The invention is not limited to institutional use, but also has practical application as a single, stand alone device in addition to its potential for becoming a built-in device. Such applications could include in-home health care and presence monitoring for the increasing number of patients who choose to have medical care provided in their own homes.

Figure 1:
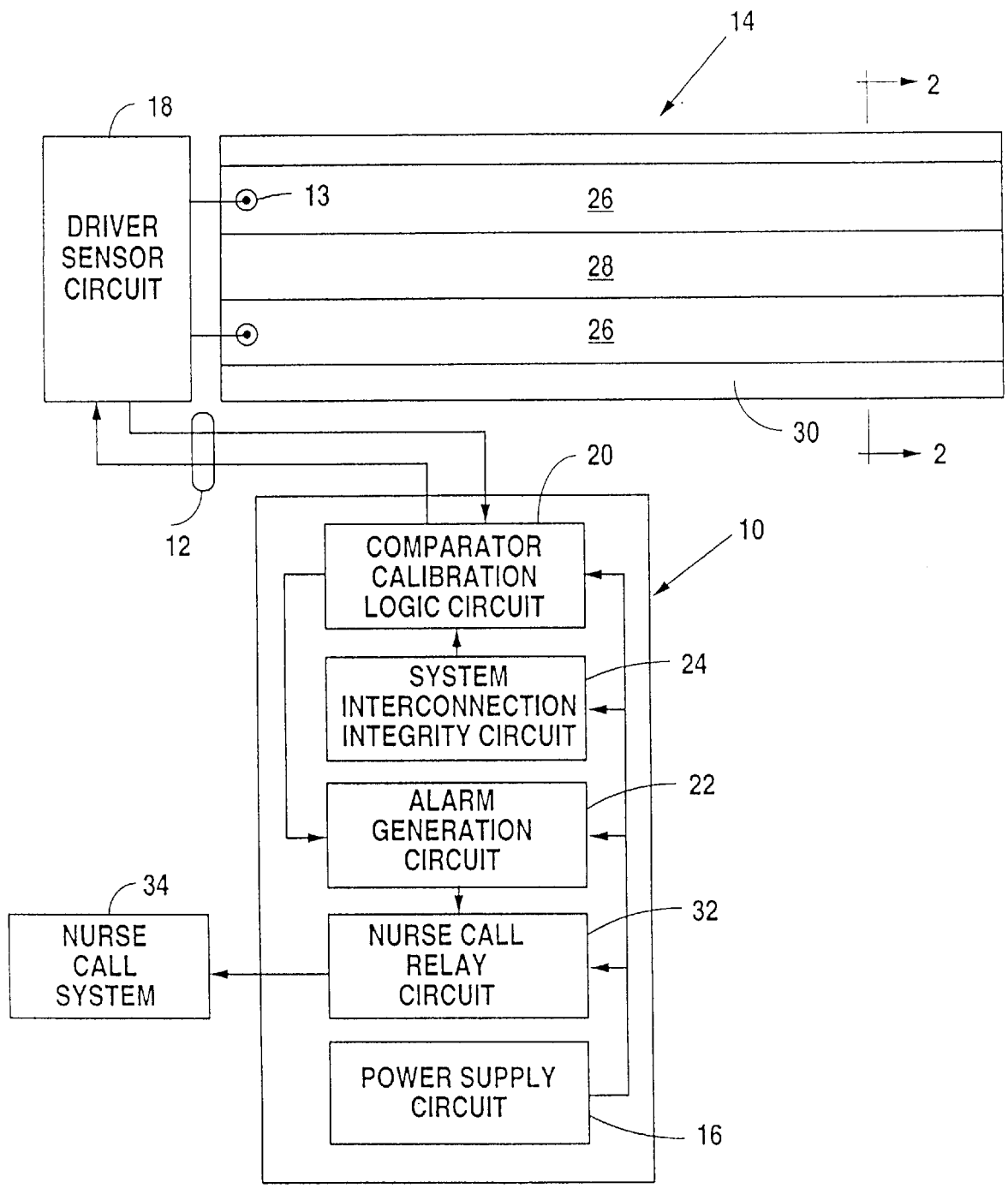
FIG. 1 is a schematic block diagram of a first preferred embodiment of the device's control/monitor module interconnected with a sensing element capacitive array.

Reference is made, therefore, to FIG. 1 for a description of a first embodiment of the current invention. FIG. 1 shows a schematic block diagram showing control/monitor module (10) for the invention interconnected through connections (12) and (13) to one embodiment of sensing element (14). Control/monitor module (10) is made up of several circuit components, including power supply (16). Power supply (16) may consist of an internal power source such as a battery, an external source with an appropriate feed to control/monitor module (10) or any other appropriate source of power known in the art.

Additional circuit components disclosed in FIG. 1 include driver/sensor circuit (18) which provides an appropriate driver current to capacitive array (26) contained within sensing element (14) and concurrently senses capacitive value changes produced within capacitive array (26) through dielectric shifts caused by the proximity or absence of the patient's body mass. Also disclosed in FIG. 1 is comparator/calibration logic circuit (20) which is preferably a microprocessor circuit containing embedded programming suitable to the applications described herein. Comparator/calibration logic circuit (20) interfaces with driver/sensor circuit (18) and alarm generation circuit (22) also contained within control/monitor module (10). In addition, comparator/calibration logic circuit (20) receives input data from system interconnection integrity circuit (24). Comparator/calibration logic circuit (20) continuously monitors the functions of driver/sensor circuit (18) both optimizing the appropriate driver current to capacitive array (26) embedded within sensing element (14) and equivalently continuously monitors and analyzes signal data from the driver/sensor circuit (18).

When the overall system is first activated comparator/calibration logic circuit (20) will determine, through the capacitive value readings it initially obtains, whether the overall system is correctly connected (through data derived from system interconnection integrity circuit (24)) and, if such is the case, then whether a patient's body mass is already proximal to sensing element (14) or if the patient's body mass is absent. From the data derived from such capacitive value readings, comparator/calibration logic circuit (20) will set appropriate capacitive value calibration parameters which, when equaled or exceeded, would indicate the presence or absence of a patient's body mass from proximal contact with sensing element (14). Due to varying environmental conditions (humidity, the presence or absence of other grounded or nongrounded structures, body mass of the patient, etc.), that the capacitive elements (26) embedded within sensing element (14) may be subject to comparator/calibration logic circuit (20) may, as required, adjust the calibration of the capacitive value change parameters.

The principle signal characteristic utilized by comparator/calibration logic circuit (20) is not a direct analysis of capacitive change value derived from sensing element (14), but rather an analysis of the ratio comparing the inherent, resting "unoccupied" capacitance of sensing element (14) examined along side a capacitive value caused through a dielectric shift within sensing element (14) when a patient's body mass comes into contact with sensing element (14). It has been demonstrated through experimentation that a suitable ratio differential that provides accurate and reliable monitoring function by the invention, should be 3 to 1 or more.

Figure 4:
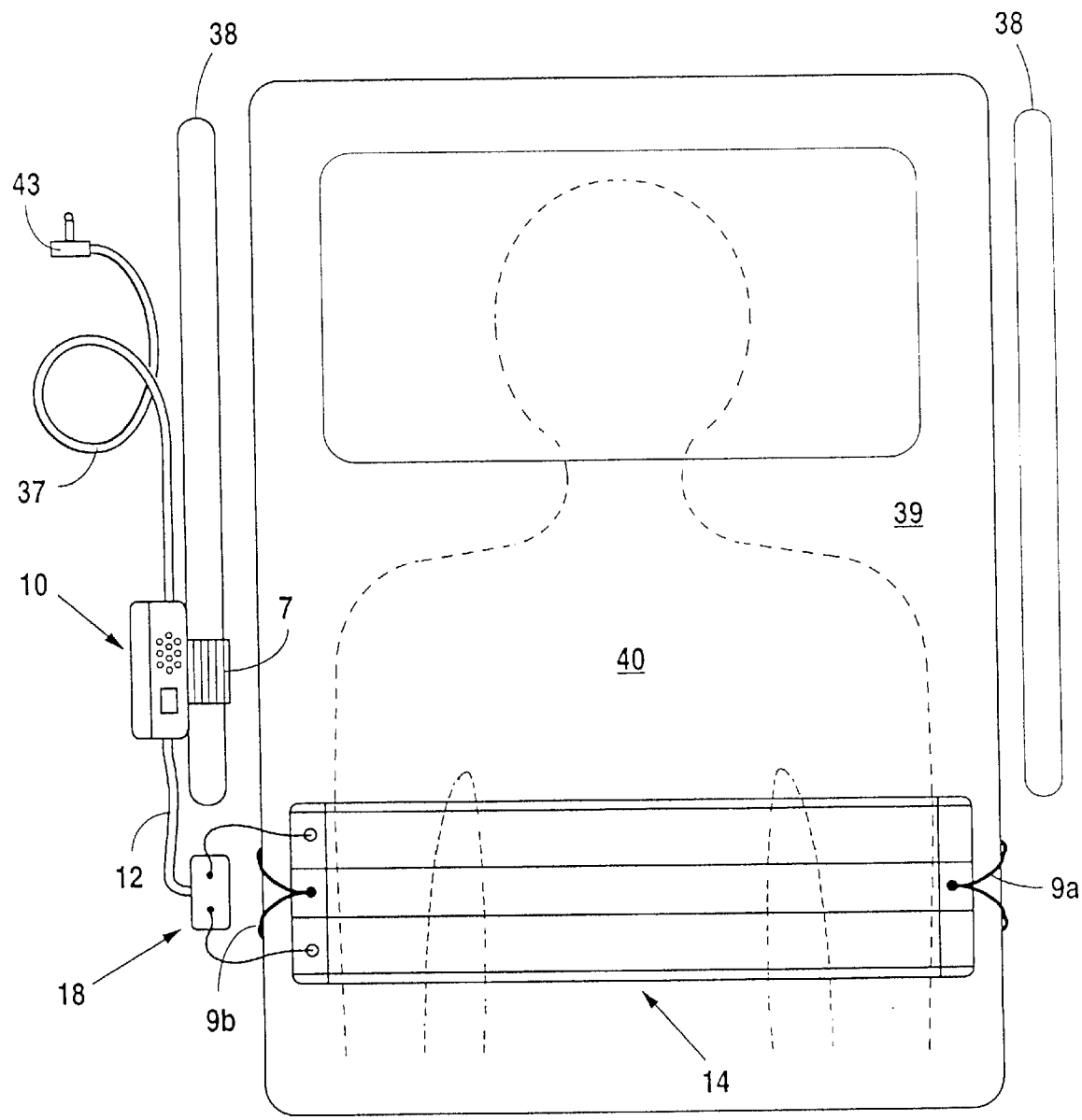
FIG. 4 is a plan view of a preferred location for the sensing element capacitive array as shown in FIG. 1 in relation to a patient in a medical bed.

The first embodiment of the invention utilizing sensing element (14), as shown in plan view in FIG. 1, has experimentally produced an inherent, resting capacitance value of approximately 15 to 20 picofarads when the capacitive array conductive elements are each 2 inches wide by 30 inches long, separated by a dielectric interspace (28) of 2 inches. This overall array is embedded in polyester substrate matrix (30) of sensing element (14) whose overall dimensions are approximately 6 inches wide by 30 inches long. The proximity application of an adult human body mass to sensing element (14) as shown in FIG. 4, has reliably produced capacitive value readings in excess of 250–300 picofarads or a ratio of 12 to 1 or more.

Existing materials utilized for capacitive array (26) manufacture may include copper film, aluminum film silver/carbon conductive ink, etc. In a preferred embodiment sensing element (14) as shown in plan view in FIG. 1 and in cross-section in FIG. 2, consists of 1 mil aluminum conductive film hermetically sandwiched between two 2.5 mil layers of inert polyester substrate (30).

Figure 2:
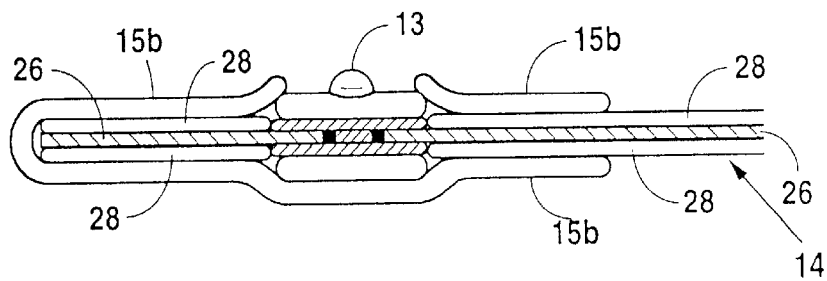
FIG. 2 is a cross-section of the sensing element capacitive array as shown in FIG. 1.

Referencing FIG. 2, the cross-sectional structure of sensing element (14) in general, and more specifically, the cross-section located at each connection point (13), is described in more detail. As indicated above, a metallic conductive film, 1 mil thick in the preferred embodiment, serves as capacitive array component (26). Capacitive array component (26) is hermetically sandwiched between two layers of inert polyester substrate (30). Connector (13) is a snap connection of the type that is typically used and referred to as an EKG connector. Attachment of snap connector (13) to conductive film (26) is made first by providing a circular window through polyester substrate (30) of a size sufficient to permit direct contact between the metallic components of snap connector (13) and the metallic conductive film, and then compressing the two-part components of snap connector (13) together so as to penetrate through conductive film (26) and compress a circular portion of conductive film (26) between the electrical contacting elements of snap connector (13). Reinforcing layer (15b) is also configured with a window through which the electrically conductive components of snap connector (13) are allowed to protrude. The remaining portion of reinforcing layer (15b) adheres to the outer surfaces and edge of the sandwiched substrate/film/substrate layers as shown. This configuration provides not only an appropriate means for reinforcing the edge of sensing element (14) but also serves to seal the edge and the area around snap connection (13).

Reference is again made to FIG. 1 for further details on the operation of the electronics of the present invention. As previously stated, when comparator/calibration logic circuit (20) achieves or exceeds a pre-defined high or low ratio limit set by its calibration circuitry in an ongoing manner, its logic circuit will determine whether control monitor module (10) enters a "resting", "monitor", or "alarm" state. Appropriate "hold" and "monitor activate override" commands to the logic circuit may be given by an external operator, such as a patient caregiver through appropriate switches integral to the circuitry. Under its own command, the logic circuit will analyze the initial absence of a patient's body mass from sensing element (14) when first activated and will enter a resting or "hold" status. On proximity application of a patient's body mass to sensing element (14) logic circuit (20) will sense the increased impedance value generated by driver/sensor circuit (18) and enter a "monitor" status mode. On removal of the patient's body mass from sensing element (14) and an equivalent appropriate ratio capacitance value decrease derived from driver/sensor circuit (18), logic circuit (20) will enter an "alarm" status mode. Should this "alarm" status exist for longer than a predetermined, operator programmed time delay, logic circuit (20) will instruct alarm generation circuit (22) to enter an "alarm" mode. The purpose of the operator programmed time delay, if required, is to prevent improper or false alarms being generated by the described device through the transient shifting by the patient of his or her body mass adjacent to sensing element (14). An "alarm" mode activation by control module (10) will trigger activity of nurse call relay circuit (32), which will in turn activate a medical facility's nurse call system (34) if so interfaced.

Should comparator/calibration logic circuit (20) ultimately require alarm generation circuit (22) to enter an alarm generation state caused by the absence of the patient's body mass from the sensing element, the alarm status so generated will be maintained, under normal circumstances, even though the patient reapplies his/her body mass to the sensing element following the generation of such an alarm. Such programming (which may be overridden by the caregiving operator) will dissuade the patient from frequently moving off and on the sensing element. Comparator/calibration logic circuit (20) may also be programmed to perform other functions as required (for instance, automatically shifting to a "monitor" mode from a "resting" or "hold" mode when the patient's body mass has been proximal to sensing element (14) for a defined period of time).

Driver/sensor circuit (18) is positioned in close attachment to sensing element (14) in order to reduce any extraneous electromagnetic field effects. Driver/sensor circuit (18) comprises circuitry appropriate for measuring the capacitance in capacitive array (26) and generating a variable frequency signal relative to the capacitance value. The variable frequency output thus encodes the capacitance value in a signal that is less susceptible to interference from extraneous fields. The signal can be provided through ordinary wire connections (12) in FIG. 1 back to control/monitor module (10).

Reference is now made to FIG. 3 for a detailed description of the structural nature of the system described schematically in FIG. 1. Sensing element (14) is structurally much as described in FIG. 1, being made of a flexible substrate (30) with embedded flexible capacitive array elements (26). Capacitive array (26) is separated by interspace (28). Substrate (30) effectively surrounds and encases capacitive array (26).

At each end of sensing element (14), as shown in FIG. 3 are reinforcing layers (15a) and (15b). These layers, as described generally above with respect to FIG. 2, serve the dual purpose of reinforcing the attachment ends of sensing element (14) and sealing these ends at the same time. At a first end of sensing element (14), reinforcing layer (15a) covers the upper and lower surfaces of sensing element (14) and wraps around its edge much in the manner described in FIG. 2 with respect to reinforcing layer (15b). Hole or slot (11a) is punched through the entire structure (five layers) and is positioned to facilitate the attachment of a means for holding sensing element (14) to the patient's bed.

Likewise, reinforcing layer (15b) is positioned at an opposite end of sensing element (14) and wraps around the edge thereof in the manner described with regard to FIG. 2. Hole or slot (11b) is punched through the layers of sensing mat (14) and provides a means for attaching this end of sensing element (14) to the patient's bed. In addition, hole or slot (11b) provides a strain-relief mechanism as described in more detail below.

Conductors (17a) and (17b) connect the array elements (26) to the electronics of the present invention through connection points (13a) and (13b). As described above, in the preferred embodiment, these connection points (13a) and (13b) constitute EKG-type snap connectors. These type of connectors provide a sufficiently rigid, yet removable electrical attachment. FIG. 3a shows an alternative preferred embodiment and function of hole or slot (11b). To facilitate a strain-relief function on conductors (17a) and (17b), hole or slot (11b) is elongated and provides an aperture through which conductors (17a) and (17b) pass before connecting to connection points (13a) and (13b). In this manner, any strain on conductors (17a) and (17b) pulls at connection points (13a) and (13b) in a direction that is less likely to result in a disconnection.

In the preferred embodiment, driver/sensor circuit (18) is encased within a small enclosure immediately adjacent connection points (13a) and (13b). It is anticipated that in order to minimize external electromagnetic field influences, conductors (17a) and (17b), which are unshielded, would be relatively short. In the preferred embodiment, conductors (17a) and (17b) are approximately 3 inches in length. As indicated and described above, driver/sensor circuit (18) converts the capacitive values measured from sensing element (14) into a frequency output that is less susceptible to external electromagnetic field interference. This frequency signal is provided by way of connector (12) to control/monitor module (10) as shown. In the preferred embodiment, connector (12) is a four-conductor telephone-type cable terminating in a removable plug insertable into an appropriate telephone-type jack in control/monitor module (10).

In the preferred embodiment, control/monitor module (10) comprises a box shell surrounding the electronics described above. On the external surface of the module enclosure is provided guard (31) which serves the dual purpose of protecting and shielding control button (19) by way of cover panel (33) and acting as an attachment point for the module through strap slots (35). The attachment of monitor module (10) to the patient's bed is described in more detail below.

In addition, control/monitor module (10) retains a plurality of LED indicators as shown to provide the user (the caregiver or nurse) with indications regarding the status of the system. According to the functions described above and below, control/monitor module (10) incorporates low battery indicator (21), check mat indicator (23), alarm indicator (25), monitor mode indicator (27) and hold mode indicator (29).

Control/monitor module (10) is connected by way of cable (37) to nurse call system connector (43). Connector (43) terminates in a standard phono jack (41) as is typically utilized in existing nurse call system connections. Connector (43) is intended to provide the electrical connection to nurse call system (34) shown above in FIG. 1.

Control/monitor module (10) in the preferred embodiment is powered by a 3 VDC power supply typically provided by two AA type alkaline or lithium batteries. The present invention may also operate off of an AC power source with an appropriate AC adaptor circuit. When operable through an AC adaptor, control/monitor module (10) incorporates an automatic battery backup switch-over circuit to maintain operation of the device in the event of AC power interruption or failure. Such battery backup systems are well known in the art.

The low battery indicator (21) shown in FIG. 3 is connected to the electronics of the present invention so as to provide two stage indications of the internal power supply. Low battery indicator (21) is configured to begin blinking when the voltage of the internal power supply falls below 2.6 VDC. This would be indicative of a non-urgent need to replace the battery within the unit. A second stage low battery indication provided at LED (21) would occur when the power supply voltage falls below 2.48 VDC, indicating a more urgent need to replace the battery. In conjunction with the blinking low battery LED, an audible signal, as well as a closing (or opening as the case may be) of the nurse call connection would occur.

It should be noted that driver/sensor circuit (18) does not require a separate power supply to convert the capacitance values measured in sensing element (14) to a frequency shift values utilized by control monitor module (10).

Control monitor module (10) is designed to operate through manipulation of a single button to control its mode and status. The LED indicators described above are intended to provide a full system visual status identification and indication means for the user. There are two separate system integrity alarms that are incorporated into the electronics described above. The first involves a disconnected mat state that causes the check mat LED, the alarm, and the nurse call system to activate when the mat is not connected to the system. A second integrity alarm occurs when an internal electronic function failure occurs. When such an internal function failure occurs, all LEDs on control/monitor module (10) are illuminated. In addition, the electronics of control/ monitor module (10) are configured so as to provide a means for indicating the presence of a battery when no LEDs are illuminated. Pushing control button (19) one time will also provide a single, short audible tone to indicate the presence of a battery within the system.

In general, control/monitor module (10) is electronically configured to provide multiple alarm tones selectable by the user or installer. Three settings that include a "no-alarm" state can be control LED and SET by a standard DIP switch positioned within the enclosure. These DIP switch settings provide the user with the ability to select the delay time (the time between the sensing of an off-the-mat condition and the initiation of the alarm) and the duration and character of the alarm once it is activated. The electronics are configured so as to permit the selection of instantaneous alarm activation once an off-the-mat condition is detected, in which case, if the patient returns to the mat, the alarm is immediately silenced. Alternatively, three, five or eight second delays between an off-the-mat condition and the alarm can be programmed. When such delays are utilized, it is preferable for the alarm to remain on even after the patient has returned to the mat.

The process of installing and activating the system shown in FIG. 3 is simple and straightforward. With the appropriate batteries installed and the connections between control/monitor module (10) and driver/sensor circuitry (18) in place, connections are made at (13a) and (13b) to sensing element (14). Three audible pulses are heard to indicate that the system has been switched on when this mat connection is made. Likewise, when this mat connection is removed, a single audible pulse indicates the system is off. Should control/monitor module (10) be connected in like manner to a pressure sensitive switch array mat, two audible pulses are triggered. Control/monitor module (10) then continues to function in conjunction with the pressure sensitive mat in a manner identical to its function with the dielectric shift sensing mat of the present invention.

In the activation process, LED indicators on the front panel flash once to indicate their function and then the single LED hold indicator (29) activates. Once a patient is placed on the mat, the system will automatically enter a monitor mode after 15 seconds. Monitor mode may alternatively be immediately activated by pushing control button (19). The system may be switched back and forth between the hold and monitor mode by repeatedly pushing control button (19).

It is anticipated that the system of the present invention can be installed with the elements shown in FIG. 3 or may be installed in conjunction with an existing nurse call activation system within the hospital. The switches within monitor control module (10) allow it to activate either a normally open or normally closed nurse call switch system.

Reference is now made to FIG. 4 for a detailed description of the placement of the apparatus of the present invention on the typical hospital bed. Bed (39) incorporates a plurality of side rails (38) that facilitate both the attachment and the use of the system of the present invention. Patient (40) is positioned on bed (39) as shown. As described above, the placement of sensing element (14) of the present invention is best made near the larger mass areas of patient (40). In FIG. 4, sensing element (14) is positioned beneath the upper torso portion of patient (40). Sensing element (14) is placed beneath a mattress sheet or mattress cover (not shown) in an area beneath the upper torso of patient (40). Sensing element (14) is positioned on and held to the mattress of bed (39) through the use of elastic straps (9a) and (9b) as shown. In an alternative embodiment, a reverse side of sensing element (14) may be provided with adhesive material that allows the removable positioning of sensing element (14) on bed (39) without permanent attachment to its surface. Various adhesives are well known in the art to permit such removable attachment of a flexible surface.

Positioned immediately adjacent to sensing element (14) is driver/sensor circuit (18). In the preferred embodiment both the enclosure and the circuitry associated with driver/sensor circuit (18) are sufficiently lightweight and flexible as to easily be suspended by connectors (17a) and (17b) along the side of mattress (39). It is anticipated that the mattress cover or mattress sheets (not shown) would partially cover driver/sensor circuit enclosure (18). Conductor (12) connects driver/sensor circuit (18) to control/monitor module (10) which is more rigidly mounted at a position near the patient on the structural components of bed (39) or on the wall adjacent to the head of the patient's bed. Attachment to the wall is effected through the use of a wall mounted bracket that appropriately engages and retains strap slots (35).

In the preferred embodiment, control/monitor module (10) is attached to bed railing (38) by means of flexible attachment strap (7). Attachment strap (7) slips through strap slots (35) (shown in FIG. 3) and attaches control/monitor module (10) to the bed in a position serviceable by caregiver personnel. It is anticipated that the caregiver would be the individual responsible for activating and monitoring the function of the system of the present invention so control/monitor module (10) is positioned on the outside of bed rail (38). Finally, as described above, connector (37), which may be an electrical cord of any reasonable length, connects the system of the present invention to existing nurse call system connections.

It is anticipated that the flexible structure of the sensing element of the present invention permits large variations in the placement for association with a particular patient. The adaptability of the electronics of the system further permits use of a single sensing element structure in a number of applications with variations in the patient body mass that is brought in proximity to the sensing element.

In addition to being installed in environments where patient monitoring systems have not been in use, the structures of the present invention lend themselves to be retrofit into existing patient monitor systems previously based upon alternate sensing mechanisms. In many cases, existing electronics are already in place that provide the link between the patient monitor and the nursers call system. It is anticipated that further embodiments and alternative applications of the present invention may be envisioned from the above description and the attached drawings. Since any number of potential applications for identifying the presence or absence of a person or other animate or inanimate object within a particular defined space may be desirable, various modifications of the sensing element and the electronics associated with its use are contemplated. Specific modifications of the geometry of the sensing element shown in the preferred embodiment are immediately discernable from the structures and geometries of the devices and environment within which the sensing element is to be placed. The particular geometries described above are appropriate primarily for patient bed configurations and could easily be adapted to be appropriate to, for example, wheelchair environments or other sitting structures. Likewise, placement of the sensing elements described, with appropriate geometry modifications, could be made in enclosures suitable for retaining animals in veterinary hospital environments. The ability of the system to constantly optimize the capacitance measurement ratio in a manner that distinguishes between occupied and unoccupied states permits significant variations in the placement of the sensing element. Such variations are anticipated and included within the scope of the description of the present invention.

I claim:

1. An apparatus for monitoring the presence of a person within a predefined space comprising:
   a. a flexible capacitance sensor, said sensor comprising a flexible substrate and a plurality of coplanar conductive elements, said conductive elements adhesively positioned in a spaced relationship on said flexible substrate;
   b. an electronic driver circuit, said driver circuit establishing a nominal voltage between said conductive elements of said capacitance sensor; and
   c. an electronic sensor circuit, said sensor circuit detecting capacitance changes within said capacitance sensor and generating an output signal having frequency variations corresponding to said capacitance changes, said sensor circuit positioned physically adjacent to said conductive elements of said capacitance sensor to minimize interfering effects from external electromagnetic fields, said capacitance changes serving to indicate the presence or absence of said person within said predefined space.

2. The apparatus of claim 1 further comprising a releasable electrical connector for making connection between said flexible capacitance sensor and said driver circuit/sensor circuit, said releasable connecter comprising a first and a second snap connector device, each of said snap connector devices comprising a male snap element compressibly attached to said conductive elements of said capacitance sensor through an aperture in said flexible substrate, and a female snap element electrically connected to said driver circuit/sensor circuit.

3. The apparatus of claim 1 further comprising:
   d. a microprocessor, said microprocessor receiving said output signal from said sensor circuit and analyzing said frequency variations to determine if said capacitance changes within said capacitance sensor are indicative of a change in the presence of said person within said predefined space, said microprocessor generating a digital signal indicating a presence or an absence of said person within said predefined space; and
   e. an alarm circuit, said alarm circuit receiving said digital signal from said microprocessor and triggering an alarm device to identify a change in the presence of said person within said predefined space.

4. The apparatus of claim 3 wherein said alarm circuit comprises an existing nurse call alert system within a hospital environment.

5. The apparatus of claim 1 wherein said electronic driver circuit and said electronic sensor circuit are incorporated into a single module positioned physically adjacent to said conductive elements of said capacitance sensor, and said microprocessor is incorporated into a module positioned physically apart from said driver circuit/sensor circuit module, and connected thereto by a length of electrical conductor.

6. An apparatus for monitoring the presence of a person within a predefined space comprising:
   a. a flexible capacitance sensor, said sensor comprising a flexible substrate and a plurality of coplanar conductive elements, said conductive elements adhesively positioned in a spaced relationship on said flexible substrate;
   b. an electronic driver circuit, said driver circuit establishing a nominal voltage between said conductive elements of said capacitance sensor;
   c. an electronic sensor circuit, said sensor circuit detecting capacitance changes within said capacitance sensor and generating an output signal having frequency variations corresponding to said capacitance changes, said sensor circuit positioned physically adjacent to said conductive elements of said capacitance sensor to minimize interfering effects from external electromagnetic fields, said capacitance changes serving to indicate the presence or absence of said person within said predefined space;
   d. a microprocessor, said microprocessor receiving said output signal from said sensor circuit and analyzing said frequency variations to determine if said capacitance changes within said capacitance sensor are indicative of a change in the presence of said person within said predefined space, said microprocessor generating a digital signal indicating a presence or an absence of said person within said predefined space; and
   e. an alarm circuit, said alarm circuit receiving said digital signal from said microprocessor and triggering an alarm device to identify a change in the presence of said person within said predefined space.

7. A patient monitor comprising:
   a. a sensor, said sensor comprising a flexible substrate and at least one planar conductive element, said sensor positioned adjacent said patient;
   b. means for establishing a nominal voltage between said conductive element and a reference;
   c. means for detecting capacitance changes within said sensor and generating an output signal having frequency variations corresponding to said capacitance changes, said detecting means positioned physically adjacent to said at least one conductive element to minimize interfering effects from external electromagnetic fields;
   d. a microprocessor, said microprocessor receiving said output signal from said detecting means and generating a digital signal indicating a presence or an absence of said patient adjacent said sensor; and
   e. means for receiving said digital signal from said microprocessor and triggering an alarm to identify a change in the presence of said patient.

* * * * *